United States Patent [19]

Tomiyama et al.

[11] Patent Number: 4,749,705
[45] Date of Patent: Jun. 7, 1988

[54] QUINAZOLINE DERIVATIVE AND ANTI-HYPERTENSIVE AGENTS

[75] Inventors: Tsuyoshi Tomiyama, Sakaki; Tomoyuki Kawai; Yumiko Ichikawa, both of Nagano, all of Japan

[73] Assignee: Kotobuki Seiyaku Co., Ltd., Nagano, Japan

[21] Appl. No.: 14,370

[22] Filed: Feb. 13, 1987

[30] Foreign Application Priority Data

Mar. 13, 1986 [JP] Japan .................. 61-53630

[51] Int. Cl.$^4$ .................. A61K 31/501; C07D 239/84; C07D 491/52
[52] U.S. Cl. .................. 514/259; 544/250; 544/283; 544/285; 544/291; 544/293
[58] Field of Search .................. 544/291, 250; 514/259

[56] References Cited

U.S. PATENT DOCUMENTS 3,574,212  4/1971  Hess .................. 544/291
4,539,323  9/1985  Mentrup et al. .................. 544/291

Primary Examiner—Glennon H. Hollrah
Assistant Examiner—James H. Turnipseed
Attorney, Agent, or Firm—Robert E. Burns; Emmanuel J. Lobato

[57] ABSTRACT

New quinazoline derivatives are disclosed, as represented by the following formula:

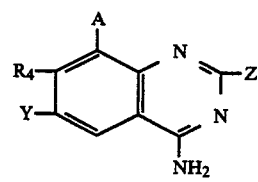

wherein A is hydrogen atom or lower alkyloxy group; $R_4$ is hydrogen atom, a lower alkyl, lower alkyloxy or a halogen atom group. Y is hydrogen atom, lower alkyloxy, sulfamoyl or Y and $R_4$, taken together, are joined to form —O—CH$_2$—CH$_2$—O—; Z is a 4-oxopiperidino, 4-thioxopiperidino, 4-oximepiperidino, 4-O-loweralkyl-oxime-piperidino, 4-O-(3-lower alkyl-2-hydroxypropyl)-oxime-piperidino, 4-O-(3-lower alkylamino-2-hydroxypropyl)-oxime-piperidino or 4-O-(3-N'-lower alkyl, N'-benzylamino-2-hydroxypropyl)-oxime-piperidino group. These compounds are useful as anti-hypertensive agents.

9 Claims, No Drawings

QUINAZOLINE DERIVATIVE AND ANTI-HYPERTENSIVE AGENTS

BACKGROUND OF THE INVENTION

This invention relates to new quinazoline derivatives and a method of their synthesis and use in medicine.

There have heretofore been used quinazoline derivatives as anti-hypertensive drugs. But it is known that orthostatic hypotention and other side effects are likely to occured at an initial dose and therefore it is desirable to obtain such anti-hypertensive drugs as are free of these side effects.

The principal object of the present invention is the provision of novel quinazoline derivatives having no such adverse reaction as mentioned above. Another object of the present invention is the provision of pharmaceutical compositions useful as anti-hypertensive agents. Still another object of the present invention is the provision of methods of preparing novel quinazoline derivatives. Other objects of the invention will become apparent from the following description.

DETAILED DESCRIPTION OF THE INVENTION

The compounds of this invention have the following general formula (I)

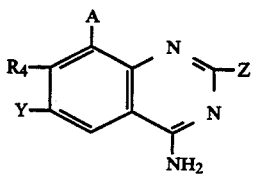

Wherein A is hydrogen or a lower alkyloxy group; $R_4$ is hydrogen, a lower alkyl, lower alkyloxy or halogen group; Y is hydrogen, a lower alkyloxy, sulfamoyl or Y and $R_4$, taken together, are joined to form —O—CH$_2$—CH$_2$—O—. Z is a 4-oxopiperidino, 4-thioxopiperidino, 4-oximepiperidino, 4-O-lower alkyl-oxime-piperidino, 4-O-(3-lower alkyl-2-hydroxypropyl)-oxime-piperidino, 4-O-(3-lower alkyl-amino-2-hydroxy-propyl)-oxime-piperidino or 4-O-(3-N'-lower alkyl, N'-benzylamino-2-hydroxypropyl)-oxime-piperidino group and pharmaceutically acceptable acid addition salt thereof. Preferred acid addition salts, for instance, include salts of mineral acid—hydrochloric acid or sulfuric acid and orgnic acid—fumaric, maleic or succinic acid and may be conveniently formed from the corresponding base by standard procedure.

In the compound of formula I, the term "lower alkyl group" designates a $C_{1-5}$ alkyl group such as a methyl, ethyl, propyl, butyl, isopropyl or isobutyl group. As lower alkoxy group, methoxy, ethoxy or propoxy groups are raised and Cl—, Br— or I— is illustrated as a halogen group. Methylamino, ethylamino, propylamino or butylamino groups are exemplified as lower alkylamino groups.

The compounds related to the general formula(I) are exemplified as follows.

(1) 2-(4-Oxopipridine-1-yl)-4-amino-6,7-dimethoxy quinazoline. (Compound 1)

(2) 2-(4-Oxopiperidine-1-yl)-4-amino-6-sulfamoyl-7-methyl quinazoline. (Compound 2)

(3) 2-(4-Oxopiperidine-1-yl)-4-amino-6-sulfamoyl-7-methoxy quinazoline. (Compound 3)

(4) 2-(4-Oxopiperidine-1-yl)-4-amino-6-sulfamoyl-7-bromo quinazoline. (Compound 4)

(5) 2-(4-Oxopiperidine-1-yl)-4-amino-6-sulfamoyl-7-chloro quinazoline. (Compound 5)

(6) 2-(4-Oxopiperidine-1-yl)-4-amino-6,7,8-trimethoxy quinazoline. (Compound 6)

(7) 2-(4-Oxopiperidine-1-yl)-4-amino-6,7-diethoxy quinazoline. (Compound 7)

(8) 2-(4-Oxopiperidine-1-yl)-4-amino-6,7-ethylenedioxy quinazoline. (Compound 8)

(9) 2-(4-Thioxopiperidine-1-yl)-4-amino-6,7-dimethoxy quinazoline. (Compound 9)

(10) 2-(4-Oximepiperidine-1-yl)-4-amino-6,7-dimethoxy quinazoline. (Compound 10)

(11) 2-(4-(O-Methyl)-oxime piperidine-1-yl)-4-amino-6,7-dimethoxy quinazoline. (Compound 11)

(12) 2-(4-(O-Ethyl)-oxime piperidine-1-yl)-4-amino-6,7-dimethoxy quinazoline. (Compound 12).

(13) 2-(4-(O-Propyl)-oxime piperidine-1-yl)-4-amino-6,7-dimethoxy quinazoline. (Compound 13)

(14) 2-(4-(O-Butyl)-oxime piperidine-1-yl)-4-amino-6,7-dimethoxy quinazoline. (Compound 14)

(15) 2-(4-(O-Isopropyl)-oxime piperidine-1-yl)-4-amino-6,7-dimethoxy quinazoline. (Compound 15)

(16) 2-(4-(O-(3-Isopropylamino-2-hydroxy)-propyl)-oxime piperidine-1-yl)-4-amino-6-sulfamoyl-7-methoxy quinazoline. (Compound 16)

(17) 2-(4-(O-(3-Isopropylamino-2-hydroxy)-propyl)-oxime piperidine-1-yl)-4-amino-6,7-dimethoxy quinazoline. (Compound 17)

(18) 2-(4-(O-(3-N'-methyl, N'-benzylamino-2-hydroxy)-propyl)-oxime piperidine-1-yl)-4-amino-6,7-dimethoxy quinazoline. (Compound 18)

(19) 2-(4-(O-(3-Isobutylamino-2-hydroxy)-propyl)-oxime piperidine-1-yl)-4-amino-6,7-dimethoxy quinazoline. (Compound 19)

(20) 2-(4-(O-(3-N'-Methyl,N'-benzylamino-2-hydroxy)-propyl)-oxime piperidine-1-yl)-4-amino-6-sulfamoyl-7-methoxy quinazoline. (Compound 20)

The above-mentioned compounds from 1 to 20 will be referred to hereinafter, as compound 1, compound 2,—compound 20 respectively.

The compound of general formula (I) can be obtained by reaction of a compound shown by the general formula (II):

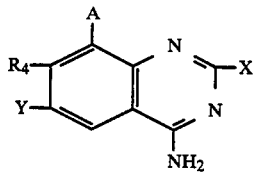

[wherein A, $R_4$, Y and Z are same as mentioned above] with a compound shown by the general formula (III):

H-Z        (III)

[wherein Z is same as mentioned above]. In case Z in formula (I) is as follows,

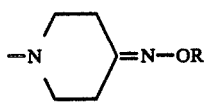

[wherein R is a lower alkyl, 3-lower alkyl amino-2-hydroxy propyl or 3-N'-lower alkyl, N'-benzyl amino-2-hydroxy propyl group] the compound of formula (I) may be prepared not only by the above mentioned method but also in the following manner. Namely, 4-oxopiperidine is used as compound of general formula (III) is reacted with a compound of the formula III and then the resulting compound of formula (IV):

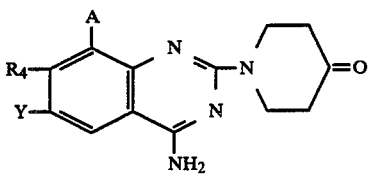

[wherein A, R$_4$ and Y are same as mentioned above] is reacted with a compound of the formula (V):

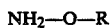

NH$_2$—O—R     (V)

The reaction of a compound of general formula (IV) with a compound of general formula (V) leads to the desired objective compound of general formula (VI).

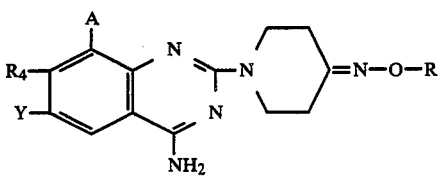

[wherein A, R$_4$, Y and R are same as mentioned above]

The reaction of the compound shown in formula (II) with that of formula (III) can generally carried out in such a solvent as methanol, ethanol, butanol, dioxane, dimethyl formamide and dimethylsulfoxide in the presence of a base. The base used in this reaction is such as triethylamine, sodium hydroxide, sodium carbonate, potassium hydroxide, potassium carbonate, sodium bicarbonate etc. or instead of using the base, 2 equivalents of compound shown in formula (III) can be used.

The reaction proceeds at room temperature or elevated temperature and the reaction of the compound shown in formula (IV) with that of formula (V) proceeds in the presence of pyridine at room temperature and whereby the compound of general formula (VI) can be obtained.

Among the compound of general formula (I), the compound that has a thioxopiperidino group of Z is obtained by reacting compound of general formula (IV) with P$_2$S$_5$ and the reaction proceeds at elevated temperature in a pyridine solution as follow.

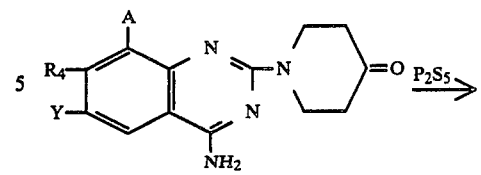

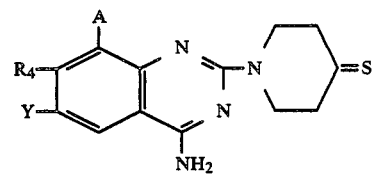

A compound of general formula (II) in which A is hydrogen, R$_4$ and Y are methoxy groups, is a known compound and can be prepared by the method described in J. Chem. Soc. 1948, 1759–66 as follows.

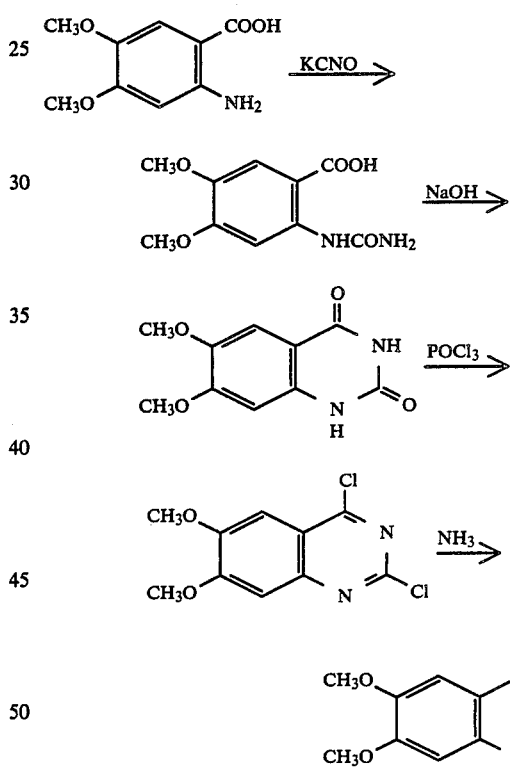

Other compounds of general formula (II) are prepared by the method mentioned above.

A compound of general formula (V), in which R is lower alkyl, is prepared as follows.

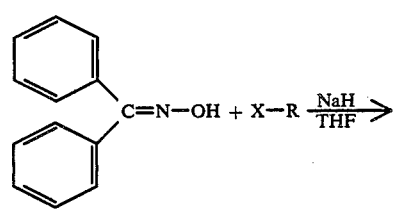

-continued

In case a compound of general formula (III) is 4-O-lower alkyl oxime piperidine, it is obtained as follows.

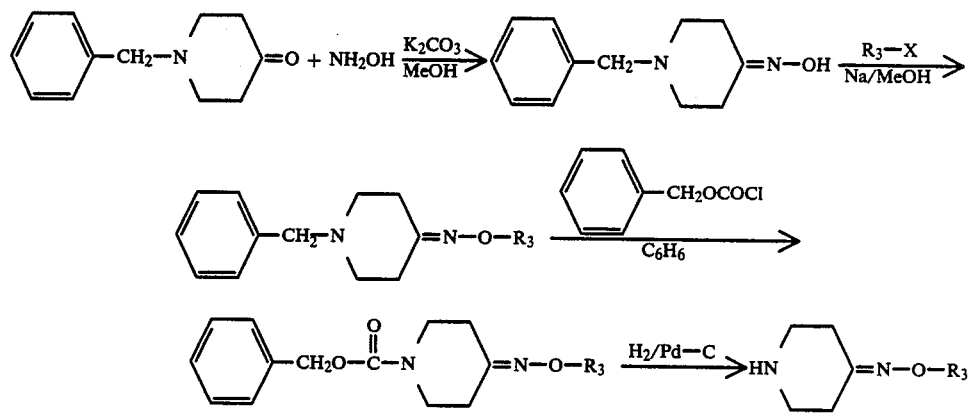

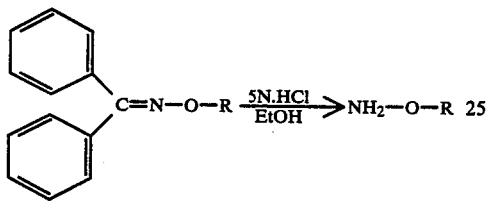

wherein X is halogen and THF is tetrahydrofuran.

A compound of general formula (V), in which R is a 3-substituted amino-2-hydroxy propyl group, is obtained by the method as shown below.

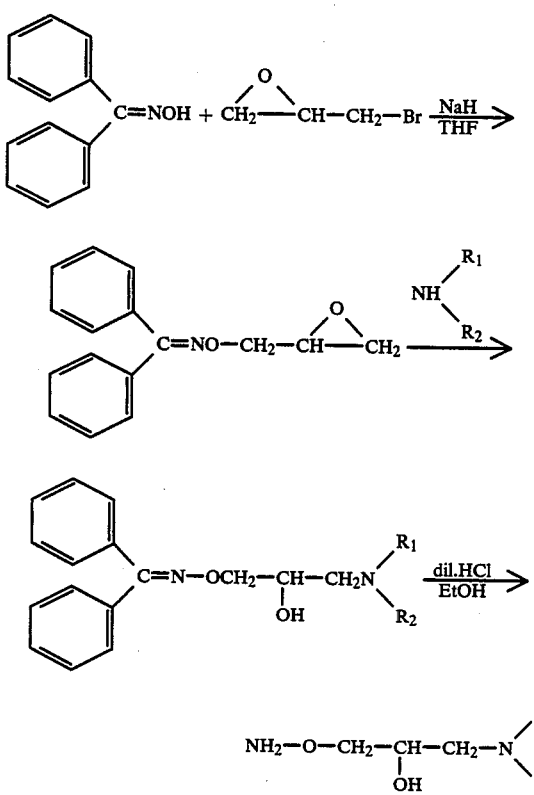

wherein R is a hydrogen or lower alkyl, and R is a lower alkyl.

wherein X is a halogen and R is a lower alkyl,

The compound of general formula (I) of this invention thus obtained show excellent anti-hypertensive activity which proves true by pharmacological tests and its therapeutic use is promising.

The compound of general formula (I) of this invention can be administered orally or parenterally. One effective dosage, depending on age and symptom, is from 5 mg to 50 mg a day for adults. Pharmacological, pharmaceutical and experimental examples of the compound of this invention are as follows.

Pharmacological example

1. α-Blocking activities

Male Wistar rats weighing 250~300 g were sacrificed and the thoracic aorta was isolated. Aortic strips were cut into helical strips about 2~3 mm in width and 10~12 mm in length. Each strip was mounted isometrically under 1.0 g of tension in a 20-ml tissue bath (37° C.) containing Krebs Ringer solution and buffled with mixed gas of 95% $O_2$ and 5% $CO_2$.

Developed tension changes were recorded using an isometric transducer (Toyo Baldwin, T7-30-240) coupled to a polygraph recorder (Nihon Kohden, RM-600).

The tissue was exposed to the compounds for 5 min before challenge with norepinephrine. The α-blocking activity was assessed by comparing with $PA_2$ (the value which was calculated according to the method of Van Rossum*. The result is shown in table 1.

TABLE 1

| Compound No. | α-Blocking Activities ($PA_2$) |
| --- | --- |
| 1 | 9.15 |
| 5 | 6.35 |
| 6 | 6.32 |
| 9 | 6.08 |
| 12 | 9.49 |
| 13 | 10.84 |
| 14 | 10.56 |
| 15 | 7.93 |
| 17 | 8.96 |
| 18 | 7.93 |
| 19 | 8.95 |

2. Antihypertensive activities

The antihypertensive activity of the compounds on anesthetized normotensive rats were tested according to the method of H. Sogabe*. Male Wistar rats weighing 200~300 g were anesthetized with urethane (1.2 g/kg i.p.). A polyethylene catheter was inserted into the femoral artery and blood pressure was measured by a transducer (Nihon Kohden, TP-200T) connected to the catheter. Heart rate was monitored by the cardiotachometers (Nihon Kohden, RT-5) and recorded simultaneously. The test compounds in physiological saline (0.1 ml/100 g B.W.) were injected via the femoral vein. The anti-hypertensive activity was assessed by comparing with $MBP_{30}$ (doses which lower mean blood pressure by 30 mmHg, mg/kg i.v.). The results are shown in table 2.

*Hirobumi Sogabe "Jikken kouketsuatsushou nyumon" P227 (Eikoudo 1968)

TABLE 2

| Compound No. | Antihypertensive Act. ($MBP_{30}$) |
|---|---|
| 1 | 0.020 |
| 9 | 3.0 |
| 12 | 0.014 |
| 13 | 0.074 |
| 15 | 0.044 |
| 17 | 0.010 |
| 18 | 0.1 |
| 19 | 0.022 |

The compounds of general formula (1) can be applied in the form of granules, tablets or capsules in the usual manner in the form of free base or in the form of their pharmaceutically acceptable acid-additions.

Pharmaceutical examples are as follows:

Pharmaceutical example 1

Tablets of following ingredients.

| Compound 13 | 5.0 g |
|---|---|
| Lactose | 90.0 g |
| Corn Starch | 15.0 g |
| Methyl Cellulose | 3.0 g |
| Magnesium Stearate | 2.0 g |
| Total | 115.0 g |

Above mentioned mixture is tableted in conventional manner to have each tablet contain 5 mg of compound 13.

Pharmaceutical example 2

Capsules of following ingredients.

| Compound 16 | 10.0 g |
|---|---|
| Lactose | 70.0 g |
| Corn Starch | 15.0 g |
| Crystalline Cellulose | 5.0 g |
| Total | 100.0 g |

Above mentioned mixture is mixed in the usual manner to have each capsule contain 10 mg of compound 16.

Reference example

2-Chloro-4-amino-6,7-dimethoxy quinazoline (1) 6,7-Dimethoxy quinazoline-2,4-dione 21 g of 2-Amino-4,5-dimethoxy benzoic acid was dissolved in 40 ml of tetrahydrofuran and 40 ml of water. To this solution 10 ml of conc. hydrochloric acid and 11.6 g of potassium cyanide were added. It was left to stand overnight and 50 g of sodium hydroxide was added. After stirring for 2 hours, the resulting precipitate was isolated by filtration. The precipitate was dissolved in 1000 ml of water and acidified with 50% sulfuric acid. The resulting crystal was isolated by filtration and 13.0 g of the desired compound was obtained. m.p. 320° C. (decomp).

(2) 2,4-Dichloro-6,7-dimethoxy quinazoline 13.0 g of 6,7-Dimethoxy quinazoline-2,4-dione was dissolved in 50.6 ml of phosphorus oxychloride and 4.5 ml of dimethylaniline and the mixture was refluxed for 5 hours. After cooling, the mixture was poured onto crushed ice and extracted with $CHCl_3$. The $CHCl_3$-extract was washed with a satd-NaCl solution and the solvent was evaporated. 9.7 g of desired compound was obtained. m.p. 156°~7° C.

(3) 2-Chloro-4-amino-6,7-dimethoxy quinazoline 8.6 g of 2.4-Dichloro-6,7-dimethoxy quinazoline was dissolved in 300 ml of tetrahydrofuran and $NH_3$-gas was introduced to the solution. After saturated with $NH_3$-gas, the reaction mixture was allow to stand for 2 days and the solvent was removed. The resulting precipitate was collected by filtration and recrystallized from methanol. 2.8 g of desired compound was obtained. m.p. 248° C. (decomp.)

EXAMPLE 1

2-(4-Oxopiperidine-1-yl)-4-amino-6,7-dimethoxyquinazoline (Compound 1)

A mixture of 1.0 g of 2-Chloro-4-amino-6,7-dimethoxyquinazoline, 1.28 g of 4-piperidone.HCl and 1.15 g of potassium carbonate in 50 ml of n-butanol was refluxed for 8 hours. and the solvent was removed under reduced pressure. To the residue was added 50 ml. of water and extracted with Ethyl acetate. Ethyl acetate extract was concentrated and the residue was washed with n-hexane. 0.98 g. of desired compound was obtained. mp. 228°~230° C. I.R. (KBr) 3350, 3200, 2900, 1700, 1645, 1595, 1570, 1500, 1465, 1260 $cm^{-1}$.

EXAMPLE 2~8

Compound 2,—compound 8 can be obtained in the same manner as the method of Example 1. These compounds are shown in table 3.

TABLE 3

| Compd. No. | Structure | m.p. (°C.) | M.S. (m/e) |
|---|---|---|---|
| 2 | $CH_3$—, $H_2NSO_2$— substituted benzene fused with N=C-N(piperidine)=O, NH₂ | 238 (dec.) | 335(M+) |

TABLE 3-continued

| Compd. No. | Structure | m.p. (°C.) | M.S. (m/e) |
|---|---|---|---|
| 3 | CH3O-, H2NSO2- substituted benzene fused with N=C(NH2)- connected to piperidine-4-one via N | 176 (dec.) | 351(M+) |
| 4 | Br-, H2NSO2- substituted benzene fused with N=C(NH2)- connected to piperidine-4-one via N | 141 (dec.) | 400(M+) |
| 5 | Cl-, H2NSO2- substituted benzene fused with N=C(NH2)- connected to piperidine-4-one via N | 218 (dec.) | 356(M+) |
| 6 | OCH3, CH3O, CH3O substituted benzene fused with N=C(NH2)- connected to piperidine-4-one via N | 189~91 | 332(M+) |
| 7 | C2H5O, C2H5O substituted benzene fused with N=C(NH2)- connected to piperidine-4-one via N | 147~8 | 331(M+) |
| 8 | Propylenedioxy substituted benzene fused with N=C(NH2)- connected to piperidine-4-one via N | 200~1 | 300(M+) |

EXAMPLE 9

2-(4-Thioxopiperidine-1-yl)-4-amino-6,7-dimethylquinazoline (Compound 9)

0.26 g. of 2-(4-oxopiperidine-1-yl)-4-amino-6,7-dimethoxyquinazoline (Compound 1) and 0.39 g. of phosphorus pentasulfide were dissolved in 15 ml. of pyridine. The mixture was warmed with stirring at 40°~50° C. for 8 hours. The solvent was removed under reduced pressure. To the residue was added $H_2O$ and pyridine was removed by codistillation in vacuum to dryness. After washing the residue with water, the residue was suspended in $H_2O$ and made basic with 10% NaOH solution. The mixture was extracted with ethylacetate and ethylacetate extract was washed with $H_2O$, dried ($Na_2SO_4$) and the solvent was removed. The residue was chromatographed on silica gel, eluting with $CHCl_3$:MeOH (10:1) 0.03 g. of desired compound was obtained. m.p. 187°~8° C.; I.R. (KBr) 3370, 2940, 1630, 1580, 1560, 1490, 1380 cm$^{-1}$. M.S (m/e) 318 (M+)

EXAMPLE 10

2-(4-Oxmepiperidine-1-yl)-4-amino-6,7-dimethoxyquinazoline.HCl (Compound 10.HCl)

A solution of 4-piperidone oxime (1.1 g) and 2-chloro-4-amino-6,7-dimethoxyquinazoline (2.4 g) in n-butanol (20 ml) was refluxed for 14 hours and after cooling, the resulting precipitate was collected by filtration and washed with EtOH. 1.66 g. of desired compound was obtained. m.p. 270° C. (decomp). I.R. (KBr) 3320, 3150, 2820, 1600, 1630, 1600, 1490, 1440 cm$^{-1}$. M.S (m/e) 300 (M+-HCl).

EXAMPLE 11

2-(4-(O-Methyl)-oximepiperidine-1-yl)-4-amino-6,7-dimethoxyquinazoline furmarate (Compound 11 fumarate)

(1) 4-(O-Methyl)-oximepiperidone

A mixture of 1-benzyl-4-piperidone (4.7 g), hydroxyamine.HCl (1.9 g) and potassium carbonate (1.7 g) was stirred for 3 hours at room temperature. The reaction mixture was filtered and the filtrate was concentrated. The residue was dissolved in $CHCl_3$, washed with $H_2O$, dried over $Na_2SO_4$ and the solvent was removed. The residue was crystallized by addition of n-hexane. After washing with n-hexane, 1-benzyl-4-oximepiperidone (2.1g) was obtained. 1-Benzyl-4-oxime-piperidone (0.6 g) thus obtained was added to a solution of EtONa (0.11 g Na in 20 ml EtOH) and $CH_3I$ (0.67 g) was added to the solution. The mixture was refluxed overnight, the solvent was evaporated and the residue was chromatographed on silica gel, eluting with $CHCl_3$:MaOH (10:1). Only 1-Benzyl-4-piperidone-oxime methylether (0.30 g) was obtained. 1-Benzyl-4-piperidone-oxime methylether (0.30 g) thus obtained was dissolved in benzene (30 ml) and benzyl oxycarbonyl chloride (0.26 g) was added to the solution and the mixture was refluxed for 16 hours. Benzene and the resulting benzylchloride was evaporated under reduced pressure. 1-Benzyloxycarbonyl-4-piperidone (0.42 g) thus obtained was dissolved in EtOH (80 ml) and conc.HCl (1 ml). The mixture was hydrogenated and filtered, and the solvent was removed at reduced pressure. 0.14 g. of desired 4-(O-Methyl)-oxime piperidone was obtained. I.R. (KBr) 3420, 3000, 2800, 1430, 1050 $cm^{-1}$. M.S. (m/e) 128 ($M^+$-HCl).

(2) Compound 11 fumarate 4-(O-Methyl)-oximepiperidone (0.14 g, obtained from (1)) and 2-chloro-4-amino-6,7-dimethoxyquinazoline (0.21 g) were dissolved in a mixture of 0.12 g of potassium carbonate and 20 ml of n-butanol. The mixture was refluxed for 1.5 hours and filtered, and the filtrate was concentrated. The Residue (0.13 g) was dissolved in MeOH and an equivelent amount of fumaric acid was added. The solvent was evaporated. The resulting precipitate was washed with ethylacetate and 0.15 g of Compound 11 fumarate was obtained. m.p. (198°~200° C.) I.R. 3400, 3150, 2950, 1640, 1600, 1530, 1490 $cm^{-1}$. M.S. (m/e) 332 ($M^+$-fumaric acid).

EXAMPLE 12

2-(4-(O-Ethyl)-oximepiperidine-1-yl)-4-amino-6,7-dimethoxyquinazoline (Compound 12)

(1) O-Ethylhydroxyamine.HCl

To a solution of benzophenone oxime (2.0 g) in 15 ml of THF was added 0.29 g of NaH and 1.3 g. of $CH_3I$ at 0° C. The mixture was refluxed for 16 hours, filtered, and evaporated. The residue was dissolved in $CHCl_3$ and washed with water and dried ($Na_2SO_4$). The solvent was evaporated. Only benzophenone oxime ethylether (2.43 g) was obtained. This benzophenone oxime ethylether (2.43 g) was dissolved in EtOH (20 ml) and 1N-HCl (20 ml). The mixture was refluxed for 30 hours. The solvent was evaporated and the residue was dissolved in water. The solution was washed with ethylacetate and the resulting aqueous solution was evaporated to dryness. 0.43 g of O-Ethylhydroxyamine.HCl was obtained.

(2) Compound 12

0.08 g of Compound 1 and 0.05 g of O-Ethylhydroxylamine.HCl were dissolved in 10 ml of pyridine. The mixture was stirred for 4 hours at room temperature. The solvent was removed under reduced pressure. The residue was dissolved in $H_2O$ and the solution was rendered alkaline with 10% NaOH solution. The mixture was extracted with $CHCl_3$ and $CHCl_3$ solution was washed ($H_2O$) and dried ($Na_2SO_4$), and evaporated. The residue was crystallized by addition of n-hexane. After washing with n-hexane, desired compound (0.07 g) was obtained. m.p. 231° C. (decomp). I.R. 3400, 3330, 2930, 2840, 1650, 1590, 1500, 1450 $cm^{-1}$. M.S. (m/e) 345 ($M^+$), 300, 233 (B.P.)

EXAMPLE 13 20

Compound 13,—Compound 20 can be obtained in the same manner as the method of Example 12. Especially 3-substituted amino-2-hydroxypropyl Compounds were prepared by reaction of 2-(4-Oxopiperidine-1-yl)-4-amino-substd.-quinazolines such as compound 1 with O-substd.-hydroxylamine. The O-substd.-hydroxylamines were obtained by reaction of benzophenone oxime with epibromohydrin and reacted with suitable amines. The resulting O-(2,3-epoxypropyl)-benzophenone derivatines were hydrolyzed to O-substd. hydroxyamine in the same manner as the method of Example 12. Objective compounds are shown in table 4.

TABLE 4

| Compd. No. | | m.p. (°C.) | M.S. (m/e) |
| --- | --- | --- | --- |
| 13 | 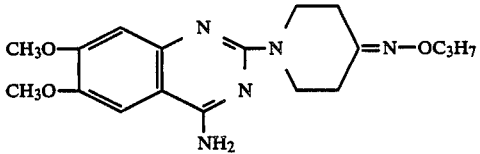 | 189~91 | 360($M^+$) |
| 14 | 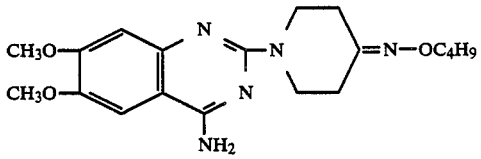 | 190~1 | 374($M^+$ + 1) |

TABLE 4-continued

| Compd. No. | | m.p. (°C.) | M.S. (m/e) |
|---|---|---|---|
| 15 | CH₃O-[benzene]-N=C(N-piperidine=N-O-CH(CH₃)₂)-N, NH₂; CH₃O- | 225~7 | 360(M⁺) |
| 16 | CH₃O-, H₂NSO₂-[benzene]-N=C(N-piperidine=N-OCH₂CH(OH)-CH₂-NHCH(CH₃)₂)-N, NH₂ | 176~8 | 463 (M⁺ − H₂O) |
| 17 | CH₃O-, CH₃O-[benzene]-N=C(N-piperidine=N-OCH₂CH(OH)-CH₂-NHCH(CH₃)₂)-N, NH₂ | 147~9 | 432(M⁺) |
| 18 | CH₃O-, CH₃O-[benzene]-N=C(N-piperidine=N-OCH₂CH(OH)-CH₂-N(CH₃)(CH₂-phenyl))-N, NH₂ | 109~111 | 495(M⁺) |
| 19 | CH₃O-, CH₃O-[benzene]-N=C(N-piperidine=N-OCH₂CH(OH)-CH₂-NHCH₂CH(CH₃)₂)-N, NH₂ | 120~2 | 447(M⁺ + 1) |
| 20 | CH₃O-, H₂NSO₂-[benzene]-N=C(N-piperidine=N-OCH₂CH(OH)-CH₂N(CH₃)(CH₂-phenyl))-N, NH₂ | 152~4 | 544(M⁺ + 1) |

What is claimed is:

1. A compound of the formula:

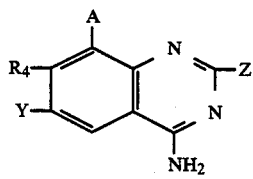

wherein:
A is hydrogen atom or a lower alkyloxy group; $R_4$ is hydrogen atom, a lower alkyl, lower alkyloxy or halogen atom group; Y is hydrogen atom, lower alkyloxy, sulfamoyl or Y and $R_4$, taken together, are joined to form —O—CH₂—CH₂—O—; Z is a 4-oxopiperidino, 4-thioxopiperidino, 4-oximepiperidino, 4-O-lower alkyl-oxime-piperidino, 4-O-(3-lower alkyl-2-hydroxypropyl)-oxime-piperidino, 4-O-(3-lower alkyl amino-2-hydroxypropyl)-oxime-piperidino or 4-O-(3-N'-lower alkyl, N'-benzylamino-2-hydroxy propyl)-oxime-piperidino group; or pharmaceutically acceptable acid addition salts thereof.

2. A compound according to claim 1 wherein $R_4$ and Y each represents a lower alkyloxy group.

3. A compound according to claim 1 wherein $R_4$ and Y, taken together, are joined to form —O—CH₂CH₂—O—.

4. A compound according to claim 1 wherein Y is a sulfamoyl group.

5. A compound according to claim 1 wherein Z represents

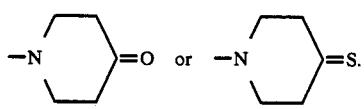

6. A compound according to claim 1 wherein Z represents a 4-oximepiperidino or 4-O-lower alkyl-oxime-piperidino group.

7. A compound according to claim 1 wherein Z represents a 4-O-(3-lower alkyl-2-hydroxypropyl)-oxime-piperidino group.

8. A compound according to claim 1 wherein Z represents a 4-O-(3-substituted amino-2-hydroxypropyl)-oxime-piperidino group.

9. An anti-hypertensive composition comprising an effective amount for treatment of hypertension of the compound defined in claim 1 combination with a pharmaceutically acceptable carrier.

* * * * *